United States Patent
Chawla

(10) Patent No.: US 10,548,943 B2
(45) Date of Patent: *Feb. 4, 2020

(54) METHOD OF TREATING LOW BLOOD PRESSURE

(71) Applicant: The George Washington University a Congressionally Chartered Not-for-Profit Corporation, Washington, DC (US)

(72) Inventor: Lakhmir S. Chawla, McLean, VA (US)

(73) Assignee: The George Washington University a Congressionally Chartered Not-for-Profit Corporation, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/439,881

(22) Filed: Jun. 13, 2019

(65) Prior Publication Data
US 2019/0374597 A1    Dec. 12, 2019

Related U.S. Application Data

(63) Continuation of application No. 16/057,366, filed on Aug. 7, 2018, now Pat. No. 10,335,451, which is a continuation of application No. 15/922,513, filed on Mar. 15, 2018, now Pat. No. 10,322,160, which is a continuation of application No. 15/870,139, filed on Jan. 12, 2018, which is a continuation of application No. 15/380,574, filed on Dec. 15, 2016, now Pat. No. 9,867,863, which is a continuation of application No. 12/639,987, filed on Dec. 16, 2009, now Pat. No. 9,572,856.

(51) Int. Cl.
*A61K 38/08*    (2019.01)

(52) U.S. Cl.
CPC .................... *A61K 38/085* (2013.01)

(58) Field of Classification Search
None
See application file for complete search history.

(56) References Cited

U.S. PATENT DOCUMENTS

| | | | |
|---|---|---|---|
| 4,330,532 A | 5/1982 | Nyeki et al. | |
| 5,216,025 A | 6/1993 | Gross et al. | |
| 5,444,067 A | 8/1995 | Kivlighn et al. | |
| 6,592,865 B2 | 7/2003 | Parry et al. | |
| 7,666,408 B2 | 2/2010 | Bachmann | |
| 9,220,745 B2 | 12/2015 | Chawla | |
| 9,457,059 B2 | 10/2016 | Tidmarsh | |
| 9,572,856 B2 | 2/2017 | Chawla | |
| 9,867,863 B2 | 1/2018 | Chawla | |
| 10,028,995 B2 | 7/2018 | Chawla | |
| 10,322,160 B2 | 6/2019 | Chawla | |
| 10,335,451 B2* | 7/2019 | Chawla | |
| 2010/0172862 A1 | 7/2010 | Correia et al. | |
| 2011/0144026 A1 | 6/2011 | Chawla | |
| 2016/0074465 A1 | 3/2016 | Tidmarsh | |
| 2016/0129072 A1 | 5/2016 | Chawla | |
| 2017/0014471 A1 | 1/2017 | Tidmarsh | |
| 2017/0095526 A1 | 4/2017 | Chawla | |
| 2017/0196931 A1 | 7/2017 | Chawla | |
| 2017/0224761 A1 | 8/2017 | Tidmarsh et al. | |
| 2018/0133282 A1 | 5/2018 | Chawla | |
| 2018/0311306 A1 | 11/2018 | Tidmarsh et al. | |

FOREIGN PATENT DOCUMENTS

| | | |
|---|---|---|
| WO | WO 2007/146900 A2 | 12/2007 |
| WO | WO 2008/059062 A1 | 5/2008 |
| WO | WO 2012/009545 A1 | 1/2012 |
| WO | WO 2014/176534 A1 | 10/2014 |
| WO | 2015/095535 A1 | 6/2015 |
| WO | WO 2016/007589 A1 | 1/2016 |
| WO | WO 2017/120438 A1 | 7/2017 |
| WO | WO 2017/120440 A1 | 7/2017 |
| WO | WO 2018/191678 A1 | 10/2018 |

OTHER PUBLICATIONS

Ryding, J. et al., "Reversal of 'Refractory Septic Shock' vby Infusion of Amrinone and Angiotensin II in an Anthracycline-Treated Patient," Chest, 107, 201-203, 1995. [Cited in parent U.S. Appl. No. 15/870,139, filed Jan. 12, 2018.].

Salemo et al., "Diagnosis, Prevention and Treatment of Hepatorenal Syndrome in Cirrhosis," Recent Advanced in Clinical Practice GUT, 2007; 56: 1310-1318. [Cited in parent U.S. Appl. No. 15/870,139, filed Jan. 12, 2018.].

Sansoe et al., "Inappropriately low angiotensin II generation: a factor determining reduced kidney function and survival in patient with decompensated cirrhosis," 2004; 40:417-423. [Cited in parent U.S. Appl. No. 15/870,139, filed Jan. 12, 2018.].

Schroeder et al., "Renal Failure in Patients with Cirrhosis of the Liver," Am J Med, 1967; 43(6): 887-96. [Cited in parent U.S. Appl. No. 15/870,139, filed Jan. 12, 2018.].

Simon et al., "Duration and magnitude of hypotension and monocyte deactivation in patients with community-acquired pneumonia," Shock, 36(6), pp. 553-559 (Dec. 2011). [Cited in parent U.S. Appl. No. 15/870,139, filed Jan. 12, 2018.].

Struthers et al., Review of aldosterone- and angiotensin II-induced target organ damage and prevention. Cardiovasc Res 2004, 61(4):663-670. [Cited in parent U.S. Appl. No. 15/870,139, filed Jan. 12, 2018.].

Thomas, V.L. et al., "Administration of Angiotensin II in refractory septic shock," Critical Care Medicine, vol. 19, No. 8, pp. 1084-1086, 1991. [Cited in parent U.S. Appl. No. 15/870,139, filed Jan. 12, 2018.].

Tremblay et al., "Effect of Hypotension Preceding Death on the Function of Lungs from Donors with Nonbeating Hearts," The Journal of Heart and Lung Transplantation, vol. 15, No. 3, pp. 260-268 (1996). [Cited in parent U.S. Appl. No. 15/870,139, filed Jan. 12, 2018.].

(Continued)

*Primary Examiner* — Satyanarayana R Gudibande
(74) *Attorney, Agent, or Firm* — Sterne, Kessler, Goldstein & Fox P.L.L.C.

(57) ABSTRACT

A method for treating a patient suffering from one of septic shock, acute kidney injury, severe hypotension, cardiac arrest, and refractory hypotension, but not from myocardial infarction, is provided. The method includes administering a therapeutically effective dose of Angiotensin II, or Ang II, to the patient.

26 Claims, No Drawings

(56) References Cited

OTHER PUBLICATIONS

Trilli et al., Lisinopril overdose and management with intravenous angiotensin II. Ann Pharmacother 1994, 28(10):1165-1168. [Cited in parent U.S. Appl. No. 15/870,139, filed Jan. 12, 2018.].
Uchino et al., Acute renal failure in critically ill patients: a multinational, multicenter study. JAMA 294:813-818, 2005. [Cited in parent U.S. Appl. No. 15/870,139, filed Jan. 12, 2018.].
Unknown Author, "NSC107678," http://www.repository.cam.ac.uk/handle/1810/88629 (Jun. 21, 2017).[Cited in parent U.S. Appl. No. 15/870,139, filed Jan. 12, 2018.].
Vaile, J.C. et al., "Angiotensin II modulates cardiovascular autonomic control in the absence of baroreflex loading," Heart, vol. 80, pp. 127-133, 1998. [Cited in parent U.S. Appl. No. 15/870,139, filed Jan. 12, 2018.].
Vincent et al., The SOFA (Sepsis-related Organ Failure Assessment) score to describe organ dysfunction/failure. On behalf of the Working Group on Sepsis-Related Problems of the European Society of Intensive Care Medicine. Intensive Care Med 1996, 22(7):707-710. [Cited in parent U.S. Appl. No. 15/870,139, filed Jan. 12, 2018.].
Vincent JL, De Backer D: Circulatory shock. N Engl J Med 2013, 369(18):1726-1734. [Cited in parent U.S. Appl. No. 15/870,139, filed Jan. 12, 2018.].
Walpole et al., BMC Public Health, 2012, 12:439. [Cited in parent U.S. Appl. No. 15/870,139, filed Jan. 12, 2018.].
Wan, L. et al., "Angiotensin II in experimental hyperdynamic sepsis," Critical Care vol. 13, No. 6, pp. 1-10, 2009. [Cited in parent U.S. Appl. No. 15/870,139, filed Jan. 12, 2018.].
Weisgerber et al., "Vasopressin analogue injection as ultimate measure for counteracting severe catecholamine-refractory poisoning by several vasodilators taken with suicidal intent," Dtsch Med Wochenschr, pp. 2189-5192 (2003). [Cited in parent U.S. Appl. No. 15/870,139, filed Jan. 12, 2018.].
Whiteley et al., Treatment of hypotension in septic shock. Lancet 1996, 347(9001):622. [Cited in parent U.S. Appl. No. 15/870,139, filed Jan. 12, 2018.].
Wilson et al., U.S. trends in CABG hospital volume: the effect of adding cardiac surgery programs. Health Aff 26:162-168, 2007. [Cited in parent U.S. Appl. No. 15/870,139, filed Jan. 12, 2018.].
Wray, G.M. et al., "Severe septic shock unresponsive to nonadrenaline," Lancet vol. 346, p. 1604, 1995. [Cited in parent U.S. Appl. No. 15/870,139, filed Jan. 12 2018.].
Yunge M. et al., "Angiotensin for septic shock unresponsive to noradrenaline," Arch Dis Child 2000, Vo. 82, pp. 388-389, 2014. [Cited in parent U.S. Appl. No. 15/870,139, filed Jan. 12, 2018.].
Ziegler et al., "Hepatorenal Syndrome: A Disease Mediated by the Intrarenal Action of Renin," Med Hypothesis, 1976; 2: 15-213. [Cited in parent U.S. Appl. No. 15/870,139, filed Jan. 12, 2018].
Sigma-Aldrich Co., Production information, Angiotensin II, human, Apr. 13, 2012. [Cited in parent U.S. Appl. No. 15/870,139, filed Jan. 12, 2018.].
Xue et al., "Sensitization of Slow Pressor Angiotensin II (ANGII) Initiated Hypertension: Induction of Sensitization by Prior ANGII Treatment," Hypertension, 59(2): pp. 459-466 (Feb. 2012). [Cited in parent U.S. Appl. No. 15/870,139, filed Jan. 12, 2018.].
Ames et al., "Prolonged Infusions of Angiotensin II and Norepinephrine and Blood Pressure, Electrolyte Balance, and Aldosterone and Cortisol Secretion in Normal Man and in Cirrhosis and Ascites," Journal of Clinical Investigation, 1965; 44(7): 1171-1186. [Cited in parent U.S. Appl. No. 15/870,139, filed Jan. 12, 2018.].
Angus et al., Epidemiology of severe sepsis in the United States: Analysis of incidence, outcome, and associated costs of care. Crit Care Med 29:1303-1310, 2001. [Cited in parent U.S. Appl. No. 15/870,139, filed Jan. 12, 2018.].
Avanzini et al., Journal of Hypertension, 2006, vol. 24, No. 12, 2377-2385. [Cited in parent U.S. Appl. No. 15/870,139, filed Jan. 12, 2018.].
Bacgenm, "Angiotensin II acetate salt," http://shop.bachem.com/h-1705.html (Mar. 31, 2017). [Cited in parent U.S. Appl. No. 15/870,139, filed Jan. 12, 2018.].

Bagshaw et al., A Multi-Centre Evaluation of the Rifle Criteria for Early Acute Kidney Injury in Critically Ill Patients. Nephrol Dial Transplant Oct. 25 (Epub): 2007. [Cited in parent U.S. Appl. No. 15/870,139, filed Jan. 12, 2018.].
Basso et al., History about the discovery of the renin-angiotensin system_ Hypertension 2001 38(6)1246-1249. [Cited in parent U.S. Appl. No. 15/870,139, filed Jan. 12, 2018.].
Busse et al., P160 "Angiotensin II may be used for the treatment of hypotension in distributive shock, but a safe and efficacious dose is unknown", Critical Care 2014, vol. 18, Supp11, http://ccforum.com/supplements/18/51, p. S57. [Cited in parent U.S. Appl. No. 15/870,139, filed Jan. 12, 2018.].
Campbell, D.J., "Do intravenous and subcutaneous angiotensin II increase blood pressure by different mechanisms?," Frontiers in Research Review: Evolving Concepts of the Renin-Angiotensin System, Clinical and Experimental Pharmacology and Physiology, 40, 560-570, 2013. [Cited in parent U.S. Appl. No. 15/870,139, filed Jan. 12, 2018.].
Chawla, L.S. et al., "Intravenous Angiotensin II for the Treatment of Hihg-output Shock (ATIIOS trial): A Pilot Study," Critical Care, vol. 18, Issue 5, Article No. 534, published on-line Oct. 6, 2014. [Cited in parent U.S. Appl. No. 15/870,139, filed Jan. 12, 2018.].
Cohn, J., et al., "Studies in Clinical Shock and Hypotension. II. Hemodynamic Effects of Norepinephrine and Angiotensin," Journal of Clinical Investigation, vol. 44, No. 9, pp. 1494-1504, 1965. [Cited in parent U.S. Appl. No. 15/870,139, filed Jan. 12, 2018.].
Correa, T.D. MD, et al., "Angiotensin II in Septic Shock: Effects on Tissue Perfusion, Organ Function, and Mitochondrial Respiration in a Porcine Model of Fecal Peritonitis," Clinical Care Mediine, vol. 42, No. 8, pp. e550-e559, 2014. [Cited in parent U.S. Appl. No. 15/870,139, filed Jan. 12, 2018.].
Daskalopoulos et al., "Effects of captopril on renal function in patients with cirrhosis and ascites" Journal of Hepatology, 1987; 4: 330-336. [Cited in parent U.S. Appl. No. 15/870,139, filed Jan. 12, 2018.].
Del Greco, F.D. MD, et al., "Clinical Experience with Angiotensin II in the Treatment of Shock," J.A.M.A., vol. 178, No. 10, pp. 130-135, 1961. [Cited in parent U.S. Appl. No. 15/870,139, filed Jan. 12, 2018.].
Dellinger, R.P. et al., "Surviving Sepsis Campaign: International Guidelines for Management of Severe Sepsis and Septic Shock: 2012," Critical Care Medicine, vol. 41, No. 2, pp. 580-657, 2013. [Cited in parent U.S. Appl. No. 15/870,139, filed Jan. 12, 2018.].
Downing, S.E., "Effects of Angiotensin II and Norepinephrine on Ventricular Performance During Oligemic Shock," The Yale Journal of Biology and Medicine, Inc., vol. 36, pp. 407-420, 1964. [Cited in parent U.S. Appl. No. 15/870,139, filed Jan. 12, 2018.].
Dworkin, Br. J. Cancer 71, 942-944, 1995. [Cited in parent U.S. Appl. No. 15/870,139, filed Jan. 12, 2018.].
Eriksson et al., "Just the Beginning: Novel Functions for Angiotensin-Converting Enzymes," Current Biology, Vo. 12, R745-752 (Oct. 29, 2012). [Cited in parent U.S. Appl. No. 15/870,139, filed Jan. 12, 2018.].
Gines et al., "Hepatorenal syndrome," Lancet, 362(9398): 1819-1827 (2003). [Cited in parent U.S. Appl. No. 15/870,139, filed Jan. 12, 2018.].
Goldsmith et al., Effect of a pressor infusion of angiotensin II on sympathetic activity and heart rate in normal humans. Circ Res 1991, 68(1):263-268. [Cited in parent U.S. Appl. No. 15/870,139, filed Jan. 12, 2018.].
Griffin et al., "Angiotensin II Causes Vascular Hypertrophy in Part by a Non-pressor Mechanism," Hypertension, 17(5):626-635 (1991). [Cited in parent U.S. Appl. No. 15/870,139, filed Jan. 12, 2018.].
Harrison-Bernard, L.M., The renal renin-angiotensin system. Adv Physiol Educ, (2009) 33(4): p. 270-274. [Cited in parent U.S. Appl. No. 15/870,139, filed Jan. 12, 2018.].
Helmy et al., "Nitric oxide mediates the reduced vasoconstrictor response to angiotensin II in patients with preascitic cirrhosis," Journal of Hepatology, 2003; 38: 44-50. [Cited in parent U.S. Appl. No. 15/870,139, filed Jan. 12, 2018.].
Heringlake et al., Renal dysfunction according to the ADQI-RIFLE system and clinical practice patterns after cardiac surgery in Ger-

(56) References Cited

OTHER PUBLICATIONS many. Minerva Anestesiol 72:645-654, 2006. [Cited in parent U.S. Appl. No. 15/870,139, filed Jan. 12, 2018.].
Jackson et al., Enalapril overdose treated with angiotensin infusion. Lancet 1993, 341(8846):703. [Cited in parent U.S. Appl. No. 15/870,139, filed Jan. 12, 2018.].
Kakavas et al., "Vasoactive support in the optimization of post-cardiac arrest hemodynamic status: From pharmacology to clinical practice," European Journal of Pharmacology 667 (2011), pp. 34-40. [Cited in parent U.S. Appl. No. 15/870,139, filed Jan. 12, 2018.].
Kanaparthi et al., Distributive Shock, Medscape Reference, Feb. 13, 2013. [Cited in parent U.S. Appl. No. 15/870,139, filed Jan. 12, 2018.].
Kopacova et al., "Hepatorenal syndrome," World Journal of Gastroenterology, 2012; 18(36): 4978-4984. [Cited in U.S. Appl. No. 15/870,139, filed Jan. 12, 2018.].
Kuitunen et al., Acute renal failure after cardiac surgery: evaluation of the RIFLE classification. Ann Thorac Surg 81:542-546, 2006. [Cited in parent U.S. Appl. No. 15/870,139, filed Jan. 12, 2018.].
LaGrange et al., Hypertension, 2003; 42:1124-1129. [Cited in parent U.S. Appl. No. 15/870,139, filed Jan. 12, 2018.].
Laragh et al., "Angiotensin II, Norepinephrine, and Renal Transport of Electrolytes and Water in Normal Man and in Cirrhosis with Ascites," Journal of Clinical Investigation, 1963; 42(7): 1179-1192. [Cited in parent U.S. Appl. No. 15/870,139, filed Jan. 12, 2018.].
Lata et al., "Hepatorenal syndrome," World Journal of Gatroenterology, 2012, 18936: 4978-4984. [Cited in parent U.S. Appl. No. 15/870,139, filed Jan. 2018.].
Le et al., "Angiotensin IV Is a Potent Agonist for Contitutive Active Human AT1 Receptors," The Journal of Biological Chemistry, VO. 277, No. 26, pp. 23107-23110 (2002). [Cited in parent U.S. Appl. No. 15/870,139, filed Jan. 12, 2018.].
Lee et al., "34-Year-Old Woman With Hypotension, Respiratory Failure, Fever, and an Abdominal Mass," West J Med, 158: 499-505 (1993). [Cited in parent U.S. Appl. No. 15/870,139, filed Jan. 12, 2018.].
Li, T. et al., "Changes in Sensitivity of Vascular Smooth Muscle to Calcium and Its Role in the Biphasic Change in Vascular Reactivity Following Hemorrhagic Shock in Rats," Chinese Critical Care Medicine, vol. 17, No. 11, pp. 647-650, Nov. 2005, English Abstract only. [Cited in parent U.S. Appl. No. 15/870,139, filed Jan. 12, 2018.].
Lianos et al., "Angiotensin-induced sodium excretion patterns in cirrhosis: Role of renal prostaglandins," Kidney International, 1982; 21: 70-77. [Cited in parent U.S. Appl. No. 15/870,139, filed Jan. 12, 2018.].
Lopes et al., Prognostic utility of RIFLE for acute renal failure in patients with sepsis. Crit Care 11:408, 2007. [Cited in parent U.S. Appl. No. 15/870,139, filed Jan. 12, 2018.].
Mayo Clinic, Septis Symptoms-Mayo Clinic, accessed on Jun. 12, 2015, availble online at: http://www.mayoclinic.org/diseases-conditions/sepsis/basics/symptoms/con-20031900. [Cited in parent U.S. Appl. No. 15/870,139, filed Jan. 12, 2018.].
McCloy et al., "Angiotensis-induced Natriuresis in Cirrhosis in the Absence of Endogenous Aldosterone Secretion," Ann Intern Med, 1966; 64(6): 1271-1276. [Cited in parent U.S. Appl. No. 15/870,139, filed Jan. 12, 2018.].
Morelli et al., Singer M: Effect of heart rate control with esmolol on hemodynamic and clinical outcomes in patients with septic shock: a randomized clinical trail. JAMA 2013, 310(16):1683-1691. [Cited in parent U.S. Appl. No. 15/870,139, filed Jan. 12, 2018.].
Morrell et al., "The Management of Severe Sepsis and Septic Shock," Infect. Dis. Clin. N. Am. 23 (2009) pp. 485-501. [Cited in parent U.S. Appl. No. 15/870,139, filed Jan. 12, 2018.].
Myburgh et al., CAT Study investigators: A comparison of epinephrine and norepinephrine in critically ill patients. Intensive Care Med 2008, 34(12):2226-2234. [Cited in parent U.S. Appl. No. 15/870,139, filed Jan. 12, 2018.].

Nassif, A.C. et al., "Angiotensin II in Treatment of Hypotensive States," J.A.M.A. vol. 183, No. 9, pp. 751-754, 1963. [Cited in parent U.S. Appl. No. 15/870,139, filed Jan. 12, 2018.].
Newby D.E. et al., "Enalapril overdose and the corrective effect of intravenous angiotensin II," Br. J. Clin Pharmacol, vol. 40, pp. 103-104, 1995. [Cited in parent U.S. Appl. No. 15/870,139, filed Jan. 12, 2018.].
Newby et al., "Peripheral vascular tone in patients with cirrhosis: role of the renin-angiotensin and sympathetic nervous systems," Cardiovascular Research, 1998; 38: 221-228. [Cited in parent U.S. Appl. No. 15/870,139, filed Jan. 12, 2018.].
Niu, C.Y. et al., "Lymphatic Hyporeactivity and Calcium Desensitization Following Hemorrhagic Shock," Shock, vol. 37, No. 4, pp. 415-423, Apr. 2012. [Cited in parent U.S. Appl. No. 15/870,139, filed Jan. 12, 2018.].
O'Brien et al., "Terlipressin for norepinephrine-resistant septic shock," Research Letters, The Lancelet, vol. 359, pp. 1209-1210 (2002). [Cited in parent U.S. Appl. No. 15/870,139, filed Jan. 12, 2018.].
Page, I.H. et al., "Angiotensin," Physiological , vol. 41, pp. 331-390, 1961. [Cited in parent U.S. Appl. No. 15/870,139, filed Jan. 12, 2018.].
Rona G: Catecholamine cardiotoxicity. J Mol Cell Cardiol 1985, 17(4):291-306. [Cited in parent U.S. Appl. No. 15/870,139, filed Jan. 12, 2018.].
Rose, J. MD, et al., "Comprison of Effects of Angiotensin and Norepinephrine on Pulmonary Circulation, Systemic Arteries and Veins, and Systemic Vascular Capacity in the Dog," Circulation, vol. 25, pp. 247-252, 1962. [Cited in parent U.S. Appl. No. 15/870,139, filed Jan. 12, 2018.].
Russell et al., VASST Investigators: Vasopressin versus norepinephrine infusion in patients with septic shock. N Engl J Med 2008, 358(9):877-887. [Cited in parent U.S. Appl. No. 15/870,139, filed Jan. 12, 2018.].
Vittorio, T., et al., "Vasopressor Response to Angiotensin II Infusion in Patients with Chronic Heart Failure Receiving β-Blockers," Circulation 290-293, (2003).
Lankadeva, Y., et al., "Urinary Oxygenation as a Surrogate Measure of Medullary Oxygenation During Angiotensin II Therapy in Septic Acute Kidney Injury," Crit Care Med, 46:e41-e48, 2018.
Rahman, "Acute Kidney Injury: A Guide to Diagnosis and Management," Am Fam Physician, 86 (7):631-636 (2012).
https//emedicine.medscape.com/article/243492-treatment, retrieved on May 14, 2018 (Year 2017).
Chawla, L., et al., "The use of angiotensin II in distributive shock," Critical Care 20(137):1-3, BioMed Central, United States (2016).
"Intravenous AII for the Treatment of Severe Hypotension in High Output Shock: A Pilot Study," NCT01393782, 3 pages (Mar. 14, 2013).
"Diagnosis and treatment for acute circulatory failure, Catecholamines' Focus on Presentation and Case Presentation," Therapeutic Research, 25(9): 1763-1773, Life Science Publishing (2004).
Kienbaum, P., et al., "Alterations in forearm vascular reactivity in patients with septic shock," Anaesthesia 63:121-128, The Association of Anaesthetists of Great Britain and Ireland, United Kingdom (2008).
Leone, M., et al., "Optimizing mean arterial pressure in septic shock: a critical reappraisal of the literature," Critical Care 19(101): 1-7, BioMed Central, United States (2015).
"Diagnosis and treatment for acute circulatory failure, Catecholamines' Focus on Presentation and Case Presentation," Therapeutic Research, 25(9):1763-1773 (2004).
Al-Merani, et al., "The Half-Lives of Angiotensin II, Angiotensin II-Amide, Angiotensin III, SAR$^1$-ALA$^8$-Angiotensin II and Renin in the Circulatory System of the Rat," J Physiol, 278: 471-490, Wiley-Blackwell, Great Britain (1978).
Bradley, S., et al., "The Hemodynamic Effects of Angiotonin in Normal Man," J Clin Invest, 20(6): 715-719, American Society for Clinical Investigation, United States (1941).
Chawla et al., "The Use of Angiotensin II in Distributive Shock," Critical Care, 20(1):137, pp. 1-3, Elsevier, Netherlands, (2016).
Collier,J.G., et al., "Comparison of Effects of Locally Infused Angiotensin I and II on Hand Veins and Forearm Arteries in Man:

(56) References Cited

OTHER PUBLICATIONS

Evidence for Converting Enzyme Activity in Limb Vessels," Clin Sci Mol Med, 47(2):189-192 Biochemical Society, United Kingdom (1974).
Conti,C., et al., "Modulation of Vascular Reactivity after Acute Calcium Antagonist Administration in Pregnant Women Moderately Sensitive to Angiotensin Infusion," J. Biol. Res., 70(10-11):243-248, PubMed Journal, United States (1994).
Cziraki, A. et al., "Quantification of Pulmonary Capillary Endothelium-bound Angiotensin Converting Enzyme Inhibition in Man," Gen Pharmacol, 35(4): 213-218, Elsevier, Netherlands (2002).
De Pasquale, N., et al., "Effect of angiotensin II on the intact Forearm Veins of Man," Circ Res, 13:239-245, American Heart Association, United States (1963).
Derrick, J., et al., "Adjunctive Use of a Biologic Pressor Agent, Angiotensin, in Management of Shock," Circulation, 25: 263-267, American Heart Association, United States (1962).
Eadington, D.W., et al., "Urinary dopamine response to angiotensin II is not abnormal in type 1 (insulin-dependent) diabetes mellitus," Nephrol Dial Transplant, 8(1):36-40 Oxford University Press, United Kingdom (1993).
Egner, B., et al., "Noninvasive Blood Pressure Monitoring: A Review," NAVC Clinician's Brief, 71-74 United States (2010).
Extended European Search Report for EP Application No. 18158219.8, dated Jun. 28, 2018.
Extended European Search Report for EP Application No. 15775357.5, dated Apr. 22, 2016.
Finnerty, F., et al., "Evaluation of the Pressor, Cardiac, and Renal Hemodynamic Properties of Angiotensin II in Man," Circ Res, 9:256-263 American Heart Association, United States (1961).
Fyhrquist, F., et al., "Renin-Angiotensin System revisited," Journal of Internal Medicine, 264: 224-236 Wiley-Blackwell, Great Britain (2008).
Ginès, Pere, et al., "Hepatorenal syndrome," The Lancet, 362: 1819-27 (2003).
Goldsmith, S., et al., "Angiotensin II and Sympathetic Activity in Patients With Congestive Heart Failure," JACC, 15(5): 1107-1113 Elsevier, Netherlands (1993).
Hou, Y., et al., "Ferulic acid inhibits vascular smooth muscle cell proliferation induced by angiotensin II," Eur J Pharmacol, 499(1-2): 85-90 Elsevier, Netherlands (2004).
Hou, J., et al., "Angiotensin II-induced Cardiac Fibrosis in the Rat Is Increased by Chronic Inhibition of Nitric Oxide Synthase," J Clin Invest, 96: 2469-2477 American Society for Clinical Investigation, United States (1995).
International Search Report and Written Opinion for International Application No. PCT/US2017/012485, Israel Patent Office, Israel, dated Apr. 27, 2017, 12 pages.
International Search Report and Written Opinion for International Application No. PCT/US2017/012487, Israel Patent Office, Israel, dated Apr. 27, 2017, 14 pages.
International Search Report and Written Opinion for International Application No. PCT/US2018/027593, Israel Patent Office, Israel, dated Jul. 22, 2018, 16 pages.
International Search Report and Written Opinion for PCT/US2014/035511, Australian Patent Office, Australia, dated Jul. 1, 2014, 8 pages.
Jones, A., et al., "The Sequential Organ Failure Assessment score for predicting outcome in patients with severe sepsis and evidence of hypoperfusion at the time of emergency department presentation," Crit. Care Med., 37: 1649-1654, Society of Critical Care Medicine and Lippincott Williams & Wilkins (2009).
Kanaide, H., et al., "Cellular Mechanism of Vasoconstriction Induced by Angiotensin II It Remains to be Determined," Circ Res, 93: 1015-1017, American Heart Association, United States (2003).
Kienbaum et al., "Alterations in Forearm Vascular Reactivity in Patients with Septic Shock," Anaesthesia, 63: 121-128, The Association of Anaesthetists of Great Britain and Ireland, United Kingdom (2008).

Kürer et al., "Hepatorenal Syndrome," Der Anaesthesist 55(1): 95-109 Springer, Berlin, De, Germany (2006).
Landry, D., et al., "Vasopressin Pressor Hypersensitivity in Vasodilatory Septic Shock," Crit Care Med, 25(8): 1279-1282 Lippincott Williams & Wilkins, United States (1997).
Lottermoser, K., et al., "Differential Effect of Acute Angiotensin II Type 1 Receptor Blockade on the Vascular and Adrenal Response to Exogenous Angiotensin II in Humans," American Journal of Hypertension, 16: 445-452 Oxford University Press, United Kingdom (2003).
Millar, E., et al., "Activity of the renin-angiotensin system in acute severe asthma and the effect of angiotensin II on lung function," Thorax, 49(5):492-495 BMJ Group, United Kingdom (1994).
Millar, E.A., et al., "Angiotensin II potentiates methacholine-induced bronchoconstriction in human airway both in vitro and in vivo," Eur. Respir. J., 8(11):1838-1841, European Respiratory Society, Switzerland (1995).
Nagamitsu, A., et al., "Elevating blood pressure as a strategy to increase tumor-targeted delivery of macromolecular drug SMANCS: cases of advanced solid tumors," Jpn J Clin Oncol, 39(11):756-766, Oxford University Press, United Kingdom (2009).
NCBI Database, PubChem Compound Database, PubChem CID: 172198.
NCBI Database, PubChem Compound Database, PubChem CID: 73354658.
Onohara, S., et al., "Intra-arterial cis-platinum infusion with sodium thiosulfate protection and angiotensin II induced hypertension for treatment of hepatocellular carcinoma," Acta Radiol, 29(2):197-202, Sage Publications, United States (1988).
Orfanos, S.E., et al., "Assay of Pulmonary Microvascular Endothelial Angiotensin-converting Enzyme In Vivo: Comparison of Three Probes," Toxicol Appl Pharmacol,124(1): 99-111, Elsevier, Netherlands (1994).
Orfanos, S., et al., "Pulmonary Capillary Endothelium-bound Angiotensin-converting Enzyme Activity in Acute Lung Injury," Circulation, 102(16): 2011-2018, American Heart Association, United States (2000).
Orfanos, S., et al., "Pulmonary Capillary Endothelium-bound Angiotensin-converting Enzyme Activity in Humans," Circulation, 99(12):1593-1599, American Heart Association, United States (1999).
Pariente, E., et al., "Acute Effects of Captopril on Systemic and Renal Hemodynamics and on Renal Function in Cirrhotic Patients with Ascites," Gastroenterology, 88(5): 1255-1259, Elsevier, Netherlands (May 1, 1985).
Pickering, T., et al., "Recommendations for blood pressure measurement in humans and experimental animals: Part 1: Blood pressure measurement in humans: a statement for professionals from the Subcommittee of Professional and Public Education of the American Heart Association Council on High Blood Pressure Research," Circulation, 111: 697-716, American Heart Association, United States (2005).
Saino, A., et al., "Intracoronary angiotensin II potentiates coronary sympathetic vasoconstriction in humans," Circulation 96(1):148-153, American Heart Association, United States (1997).
Swartz et al., "Converting Enzyme Inhibition in Essential Hypertension: The Hypotensive Response does Not Reflect only Reduced Angiotensin II Formation," Hypertension, 1: 106-111, American Heart Association, United States (1979).
Vincent, R., et al., "Prophylactic angiotensin II infusion during spinal anesthesia for elective cesarean delivery," Anesthesiology, 88(6):1475-1479, Lippincott Williams & Wilkins, United States (1998).
Vos, P., et al., "Efficacy of intrarenal ACE-inhibition estimated from the renal response to angiotensin I and II in humans," Kidney Int, 47(1):274-281, Elsevier, Netherlands (1995).
Vos, P., et al., "The origin of urinary angiotensins in humans," J Am Soc Nephrol, 5(2):215-223, American Society of Nephrology, United States (1994).
Wadei, H., et al., "Hepatorenal Syndrome: Pathophysiology and Management," Clin J Am Soc Nephrol, 1: 1066-1079, American Society of Nephrology, United States (2006).

(56) References Cited

OTHER PUBLICATIONS

Ware, L., et al., "The Acute Respiratory Distress Syndrome," N Engl J Med, 342(18):1334-1349, Massachusetts Medical Society, United States (2000).
Weber, K., "Extracellular matrix remodeling in heart failure: a role for De Novo angiotensin II generation," Circulation, 96(11):4065-4082, American Heart Association, United States (1997).
Abuelo, J., "Normotensive Ischemic Acute Renal Failure," N Engl J Med, 357(8):797-805, Massachusetts Medical Society, United States (2007).
Boehm, "Angiotensin-Converting Enzyme 2—A New Cardiac Regulator," N Engl J Med, 347(22): 1795-1797, Massachusetts Medical Society, United States (2002).
Oney, T., et al., "Effect of angiotensin infusion during pregnancy on fetal heart rate and on fetal activity," Eur. J. Obstet. Gynecol. Reprod. Biol.;13(3):133-137, Elsevier, Netherlands (1982).
Catanzaro F., et al., "Angiotensin-Infusion Test. Correlation with renin activity in peripheral venous blood," Arch Intern Med. ;122(1):10-17, American Medical Association, United States (1968).
Cook C.M., et al., "Maternal angiotensin sensitivity and fetal Doppler umbilical artery flow waveforms," Br J Obstet Gynaecol.; 98(7):698-702, Wiley & Sons, United States (1991).
Fridman K.U., et al., "Influence of AT1 receptor blockade on blood pressure, renal haemodynamics and hormonal responses to intravenous angiotensin II infusion in hypertensive patients," Blood Press. 11(4):244-252, Taylor & Francis, United Kingdom (2002).
Gordon R.D., et al., "A renin-secreting tumour sensitive to changes in central blood volume (presumably via sympathetics) but not to circulating angiotensin II," Clin Exp Pharmacol Physiol. 17(3):185-189, Wiley & Sons, United States (1990).
Katayama K., et al., "Dynamic determinants of left ventricular early diastolic filling in old myocardial infarction," Jpn Circ J. 56(7):750-758, Japanese Circulation Society, Japan (1992).
Larsson P.T., et al., "Acute effects of angiotensin II on fibrinolysis in healthy volunteers," Blood Coagulation Fibrinolysis 10(1):19-24, Lippincott Williams and Wilkins, United Kingdom (1999).
Matsuda Y., et al., "Change of left atrial systolic pressure waveform in relation to left ventricular end-diastolic pressure," Circulation 82(5):1659-1667, AHA Journals, United States (1990).
Rouine-Rapp K., et al., "Effect of enalaprilat on postoperative hypertension after surgical repair of coarctation of the aorta," Pediatr Crit Care Med. 4(3):327-332, Society of Critical Care Medicine, United States (2003).
Schachinger H., et al., "Angiotensin II decreases the renal MRI blood oxygenation level-dependent signal. Hypertension," 47(6):1062-1066, American Heart Association, United States (2006).
Seidelin P.H., et al., "The effect of angiotensin II on haemodynamic and plasma noradrenaline responses to tyramine infusion in man," Eur J Clin Pharmacol. 41(2):119-123, Springer Science +Business, Germany (1991).
Vingerhoedt N.M., et al., "Haemodynamic and pulse wave responses to intravenous infusions of angiotensin II during chronic telmisartan therapy in normal volunteers," J Renin Angiotensin Aldosterone Syst. 4(4):244-248, Sage Publications, United States (2003).
Widgren B.R., et al., "Low-dose angiotensin II increases glucose disposal rate during euglycemic hyperinsulinemia," Am J Hypertens. 6(10):892-895 Oxford University Press, United Kingdom (1993).
Gordon R.D., et al., "Angiotensin-responsive aldosterone-producing adenoma masquerades as idiopathic hyperaldosteronism (IHA: Adrenal hyperplasia) or low-renin essential hypertension," J Hypertens Suppl. 5(5):S103-S106, Wolters Kluwer, United Kingdom (1987).
Gordon R.D., et al., "A new Australian kindred with the syndrome of hypertension and hyperkalaemia has dysregulation of atrial natriuretic factor," J Hypertens 6(Suppl. 4):S323-S326, Wolters Kluwer, United Kingdom (1988).
McGibney D., et al., "Observations on the mechanism underlying the differences in exercise and isoprenaline tachycardia after cardioselective and non-selective beta-adrenoceptor antagonists," Br J Clin Pharmacol. 15(1):15-19, Wiley-Blackwell, United Kingdom (1983).

Merillon J.P., et al., "Forward and backward waves in the arterial system, their relationship to pressure waves form," Eur Heart J. 4(Suppl G):13-20, Oxford University Press, United Kingdom (1983).
Ogihara T., et al., "Clinical efficacy and tolerability of candesartan cilexetil," and "Discussion 1 New refinements in the approach to hypertension management," J Hum Hypertens. 13(Suppl 1):S27-S31 and S33-S34, Nature Publishing Group, United Kingdom (1999).
Shen W.F., et al., "Evaluation of relationship between myocardial contractile state and left ventricular function in patients with aortic regurgitation," Circulation 71(1):31-38, AHA Journals, United States (1985).
Sowers J.R., et al., "Effects of dietary sodium on circadian rhythm and physiological responses of 18-hydroxycorticosterone," Clin Sci (Lond). 64(3):295-301, Portland Press, United Kingdom (1983).
Woodland E., et al., "Hypertension corrected and aldosterone responsiveness to renin-angiotensin restored by long-term dexamethasone in glucocorticoid-suppressible hyperaldosteronism," Clin Exp Pharmacol Physiol. 12(3):245-248, John Wiley $ Sons, United States (1985).
Bentsen N., et al., "Chronically impaired autoregulation of cerebral blood flow in long-term diabetics," Stroke 6(5):497-502, American Heart Association, United States (1975).
Cokkinos D.V., et al., "Constancy of pressure-rate product in pacing-induced angina pectoris," Br Heart J. 38(1):39-42, BMJ Group, United Kingdom (1976).
Enevoldsen E.M., et al., "Autoregulation and CO2 responses of cerebral blood flow in patients with acute severe head injury," J Neurosurg. 48(5):689-703, American Association of Neurological Surgeons, United States (1978).
Fraser R., et al., "The acute effect of angiotensin II on adrenal and anterior pituitary function in normal subjects and subjects with primary hyperaldosteronism," Prog Biochem Pharmacol. 17:14-19, Karger Publishers, Switzerland (1980).
Goldsmith S.R., et al., "Angiotensin II and sympathetic activity in patients with congestive heart failure," J Am Coll Cardiol. 1993;15(5):1107-1113, Elsevier, Netherlands (1993).
Hogewind B.L., et al., "Bartter's syndrome: An autosomal recessive disorder? Study of four patients in one generation of the same pedigree and their relatives," Acta Med Scand. 209(6):463-467, John Wiley & Sons, United States (1981).
Kaulhausen H., et al., "Decrease of vascular angiotensin sensitivity by L-dopa during human pregnancy," Am J Obstet Gynecol. 140(6):671-675, Elsevier, United States (1981).
Schaison G., et al., "Angiotensin and adrenal steroidogenesis: Study of 21-hydroxylase-deficient congenital adrenal hyperplasia," J Clin Endocrinol Metab., 51(6):1390-1394, Endocrine Society, United States (1980).
Semple P.F., et al., "Suppression of plasma ACTH concentration by angiotensin II infusion in normal humans and in a subject with a steroid 17 alpha-hydroxylase defect," Clin Endocrinol (Oxf). 10(2):137-144, John Wiley & Sons, United States (1979).
Speckart P., et al., "The effect of angiotensin II and indomethacin on immunoreactive prostaglandin "A" levels in man," Prostaglandins. 1976;11(3):481-488, Elsevier, Netherlands (1976).
Ahmed S.S., et al., "The effect of angiotensin on myocardial contractility," J Clin Pharmacol, 15(4 Pt 1):276-285, John Wiley & Sons, United States (1975).
Brown M.A., et al., "The effects of intravenous angiotensin II upon blood pressure and sodium and urate excretion in human pregnancy," J Hypertens., 6(6):457-464, Lippincott Williams & Wilkins, United States (1988).
Frolich J.C., et al., "Urinary prostaglandins. Identification and origin," J Clin Invest, 55(4):763-770, American Society for Clinical Investigation, United States (1975).
Henriksen O., et al., "The effect of induced arterial hypertension upon regional blood flow in subcutaneous tissue in patients with arterial insufficiency of the legs," Scand J Clin Lab Invest., 35(2):115-120, Taylor & Francis, United Kingdom (1975).
Koch B., et al., "The influence of angiotensin infusion on the urine composition in individual kidney function tests," Can Med Assoc J., 104(10):905-907, Canadian Medical Association, Canada (1971).

(56) References Cited

OTHER PUBLICATIONS

Mehrotra, M.P., et al., "Angiotensin Infusion Test in the Diagnosis of Renal Hypertension," Journal of the Association of Physicians of India 22(4):289-292, Association of Physicians of India, India (1974).
Mendelsohn F.A., et al., "Renin, angiotensin II, and adrenal corticosteroid relationships during sodium deprivation and angiotensin infusion in normotensive and hypertensive man," Circ Res. 31(5):728-739, Lippincott Williams & Wilkins, United States (1972).
Oelkers W., et al., "Arterial angiotensin II and venous immunoreactive material before and during angiotensin infusion in man," Clin Sci. 43(2):209-218. Portland Press, United Kingdom (1972).
Parmley W.W., et al., "Dissociation between indices of pump performance and contractility in patients with coronary artery disease and acute myocardial infarction," Chest. 67(2):141-146, American College of Chest Physicians, United States (1975).
Payne R.M., et al., "Comparison of isometric exercise and angiotensin infusion as stress test for evaluation of left ventricular function," Am J Cardiol. 31(4):428-433, Elsevier, Netherlands (1973).
Rado J.P., et al., "Studies on the sites of action of ethacrynic acid and furosemide during angiotensin infusion," J Clin Pharmacol 10(6):375-381, John Wiley & Sons, United States (1970).
Ronan J.A., Jr, et al., "The angiotensin infusion test as a method of evaluating left ventricular function," Am Heart J. 89(5):554-560, Elsevier, Netherlands (1975).
Rado J.P., et al., "Effects of ethacrynic acid on specific renal functions without and during angiotensin infusion in man," Arch Int Pharmacodyn 186(1):142-154, Elsevier, Netherlands (1970).
Fukuchi, S., and Nakajima, K., "Diagnostic Value of Plasma Renin Activity and Plasma Angiotensin II in Renovascular Hypertension," Japanese Circulation Journal 39(7):823-827, Kyoto, Japanese Circulation Society(1975).
Brod, J., et al., "Comparison of Haemodynamic Effects of Equipressor Doses of Intravenous Angiotensin and Noradrenaline in Man," Clinical Science 36(2):161-172, Portland Press on behalf of the Medical Research Society and the Biochemical Society, United Kingdom (1969).
Genest, J., "The Value of the Angiotensin Infusion Test in the Diagnosis of True Renovascular Hypertension," American Heart Journal 76(4):443-444, Mosby, United States(1968).
Jezek V., et al., "Haemodynamic Reaction to Exercise and Increased Afterload in the Detection of Right Heart Failure in Pulmonary Diseases," Cor et Vasa 22(4):272-280, Elsevier, Amsterdam (1980).
Spark, R.F., et al., "Activation of Aldosterone Secretion in Primary Aldosteronism," The Journal of Clinical Investigation 48(1):96-104, American Society for Clinical Investigation, United States(1969).
Oelkers, W., et al., "Effect of Prolonged Low-Dose Angiotensin II Infusion on the Sensitivity of Adrenal Cortex in Man," Circulation Research 36 and 37 (Suppl 1):I49-I56, Lippincott Williams & Wilkins, United States(1975).

Klemm, S.A., et al., "Altering Angiotensin Levels by Administration of Captopril or Indomethacin, or by Angiotensin Infusion, Contributes to an Understanding of Atrial Natriuretic Peptide Regulation in Man," Clinical and Experimental Pharmacology and Physiology 15(4):349-355, Wiley-Blackwell, Oxford, England (1988).
Chobanian, A.V., et al., "The Seventh Report of the Joint National Committee on Prevention, Detection, Evaluation, and Treatment of High Blood Pressure: The JNC 7 report," Journal of the American Medical Association 289(19):2560-2572, American Medical Assn., United States (2003).
Bianco, J.A., et al., "Angiotensin Infusion Effects on Left Ventricular Function. Assessment in Normal Subjects and in Patients with Coronary Disease," Chest 77(2):172-175, Elsevier, United States (1980).
Merillon, J.P., et al., "Aortic Input Impedance in Normal Man and Arterial Hypertension: It's Modification during Changes in Aortic Pressure," Cardiovascular Research 16(11):646-656, Oxford Journals, Oxford (1982).
Sluiter, H.E., et al., "The Natriuretic Effect of the Dihydropyridine Calcium Antagonist Felodipine: A Placebo-Controlled Study Involving Intravenous Angiotensin II in Normotensive Volunteers," Journal of Cardiovascular Pharmacology 10(Suppl 10):S154-S161, Lippincott Williams & Wilkins, United States (1987).
"Angiotensin in Septic Kidney Injury Trial," accessed on Jan. 8, 2019, available online at https://anzctr.org.au/Trial/Registration/TrialReview.aspx?id=2037&isClinicalTrial=True, 6 pages (Aug. 7, 2008).
"Angiotensin in Septic Kidney Injury Trial (ASK-IT)," accessed on Jan. 8, 2019, available online at https://clinicaltrials.gov/ct2/show/NCT00711789, 7 pages (Jul. 9, 2008).
Badin, J. et al., "Relation between mean arterial pressure and renal function in the early phase of shock: a prospective, explorative cohort study," Critical Care, 15:R135 (2011).
Ferreira, F., et al., "Serial Evaluation of the SOFA Score to Predict Outcome in Critically Ill Patients," JAMA, 286(14): 1754-1758 (2001).
Lehman, Li-wei, et al., "Hypotension as a Risk Factor for Acute Kidney Injury in ICU Patients," Computing in Cardiology, 37:1095-1098 (2010).
Khanna, A., et al., "Angiotensin II for the Treatment of Vasodilatory Shock," New England Journal of Medicine, 377(5):419-430 (2017).
Tumlin, J., et al., "Outcomes in Patients with Vasodilatory Shock and Renal Replacement Therapy Treated with Intravenous Angiotensin II," Critical Care Medicine, 46(6):949-957 (2018).
Extended European Search Report for European Application No. 17736407.2, European National Stage Application of PCT/US2017/0120438, European Patent Office, Germany, dated Jul. 2, 2019, 7 pages.
Zambelli, V., et al., "Angiotensin-(1-7) improves oxygenation, while reducing cellular infiltrate and fibrosis in experimental Acute Respiratory Distress Syndrome," Intensive Care Medicine Experimental, 3(8): pp. 1-17 (2015).

* cited by examiner

METHOD OF TREATING LOW BLOOD PRESSURE

CROSS-REFERENCE TO RELATED APPLICATIONS

This patent application is a continuation of U.S. patent application Ser. No. 16/057,366, filed Aug. 7, 2018 (now U.S. Pat. No. 10,335,451), which is a continuation of U.S. patent application Ser. No. 15/922,513, filed Mar. 15, 2018 (now U.S. Pat. No. 10,322,160), which is a continuation of U.S. patent application Ser. No. 15/870,139, filed Jan. 12, 2018, which is a continuation of U.S. patent application Ser. No. 15/380,574, filed Dec. 15, 2016 (now U.S. Pat. No. 9,867,863), which is a continuation of U.S. application Ser. No. 12/639,987, filed Dec. 16, 2009 (now U.S. Pat. No. 9,572,856), the entire contents all of which are hereby incorporated by reference.

FIELD OF THE INVENTION

The present teachings relate to a therapeutic regimen for patients suffering from at least one of septic shock, acute kidney injury, severe hypotension, cardiac arrest, and refractory hypotension.

BACKGROUND OF THE INVENTION

Severe sepsis is the leading cause of acute kidney injury ("AKI") and its incidence is increasing.

The two leading clinical conditions associated with AM are sepsis and cardiac surgery. In the largest epidemiologic study to date (>120,000), Bagshaw et al. found that AKI occurred in 36% of intensive care unit patients and that the most common primary diagnosis was sepsis. Similarly, in a large international observational study of AKI requiring renal replacement therapy (RRT), approximately 50% of subjects had sepsis. Direct comparisons of incidence of AKI arising from sepsis vs. cardiac surgery have not been made but two studies in cardiac surgery found incidence rates of 16% and 19% while the incidence in patients with sepsis was twice as great. Furthermore, while the rates of cardiac surgery are steadily declining, sepsis incidence continues to climb. Severe sepsis currently affects more than 750,000 Americans each year and the incidence rises exponentially with age, suggesting that the number of cases will rise in coming years as baby boomers age.

Patients with septic shock who require high dose vasopressors have a mortality of over 80%. Currently, no specific type of vasopressor (e.g. norepinephrine, vasopressin, dopamine) has been shown to improve outcome. Importantly, patients on high dose catecholamines (e.g., dopamine, epinephrine, norepinephrine) for septic shock often develop tachyphylaxis, limiting the utility of these agents in the sickest patients. Vasopressin, which has been used as an adjuvant with cathecholamines, has not been shown to improve outcomes in patients with septic shock. In the subset of patients whose mean arterial pressure cannot be maintained with current vasopressors, septic shock is uniformly fatal.

Accordingly, there exists a need for the addition of an effective drug for the treatment of hypotension that does not have the deleterious effects of the present range of treatments.

SUMMARY OF THE INVENTION

The present teachings disclose a method of treating a patient suffering from low blood pressure.

According to an embodiment of the present teachings, a method of treating a patient suffering from low blood pressure is provided. The patient can suffer from one of septic shock, acute kidney injury, severe hypotension, and refractory hypotension, but not from myocardial infarction. The method can comprise administering a therapeutically effective dose of Angiotensin II ("Ang II") to the patient.

The dose of Angiotensin II can be administered at a rate of between about 5 ng/kg/min to about 100 ng/kg/min. The dose of Angiotensin II can be administered at a rate of between about 10 ng/kg/min to about 50 ng/kg/min. The dose of Angiotensin II can be administered at a rate of between about 20 ng/kg/min to about 40 ng/kg/min.

The dose administration can last from about 0.25 hours to about 120 hours. The dose administration can last from about 1 hour to about 7 hours. The dose administration can last from about 2 hour to about 6 hours. The dose administration can last from about 3 hours to about 5 hours.

Additional features and advantages of various embodiments will be set forth, in part, in the description that follows, and, in part, will be apparent from the description, or may be learned by practice of various embodiments. The objectives and other advantages of various embodiments will be realized and attained by means of the elements and combinations particularly pointed out in the description herein.

It is to be understood that both the foregoing general description and the following detailed description are exemplary and explanatory only, and are intended to provide an explanation of various embodiments of the present teachings.

DETAILED DESCRIPTION OF THE PREFERRED EMBODIMENTS

Ang II is degraded to angiotensin III in a patient, having a half life of a few minutes. Ang II is a direct vasoconstrictor by activating angiotensin I receptors, enhancing peripheral noradrenergic neurotransmission, increasing sympathetic discharge (CNS), and releasing catecholamines from the adrenal medulla.

Administration of Ang II to patients suffering from at least one of septic shock, acute kidney injury, severe hypotension, cardiac arrest, and refractory hypotension can have adverse side effects, including ischemia, such as, for example, mesenteric ischemia, that damage internal organs. The present teachings disclose a therapeutic regimen of Ang II at doses below that where adverse side effects, such as ischemia, are seen. Furthermore, the therapeutic regimen of Ang II disclosed in the present teachings can act as an adjuvant and lower the effective doses of other therapies, including administration of vasopressin and catecholamine.

The therapeutic regimen disclosed herein can be started within, for example, 1 hour, 2 hours, 4 hours, 6 hours, or 12 hours after onset of acute symptoms.

Example I

A dose study was designed to determine the feasibility of Ang II as a treatment for sepsis related hypotension.

A 20 patient randomized blinded study in the treatment of sepsis related hypotension was proposed. Patients suffering from septic shock receiving >15 mcg/min of norepineprhine are eligible. Patients are randomized to Ang II or norepinephrine in a blinded fashion. There are 10 patients in each arm. Norepinephrine is used as a control instead of a true placebo, because the blood pressure rising effects of Ang II would defeat the blinding intent.

All patients have the treatment of vasopressors titrated to a mean arterial pressure (MAP) of 65 mm of Hg. Patients are then randomized to a control group or arm, or an interventional group or arm treated with Ang II. Patients randomly assigned to the control group are administered with norepinephrine starting at 5 mcg/min, and can be titrated up to 7.5 mcg/mink, and then to 10 mcg/min. Patients in the interventional arm are administered Ang II starting at a dose of about 20 ng/kg/min. Additionally, the dose can then be titrated up to about 30 ng/kg/min. Furthermore, the dose can then be titrated up to about 40 ng/kg/min. The intervention can last for about 4 hours.

Each patient in the interventional group is started with the assigned starting dose. After the first hour, if the patient is still requiring standing norepinephrine, the dose of the control and interventional drugs can be increased 50%. After the second hour, if the patient is still requiring a standing dose of norepinephrine, the control and interventional drugs can be increased again to twice the initial dose. At the end of 4 hours, the study drug will be titrated off over 30 minutes.

In the two hours before the initiation of the study drug, all urine is collected. The urine collections are continued for a total duration of nine (9) hours. Blood is drawn at the initiation of the study, four (4) hours thereafter, and then seven (7) hours after. This involves a total of three (3) blood draws of 7 cc of blood per draw for a total of 21 cc of blood. Blood is examined for serum chemistry and serum lactate. In this same time period, demographic and clinical data are collected. Creatinine clearance will be calculated for the pre-study, study, and post-study periods.

Blood pressure of each patient is monitored continuously from about two (2) hours before initiation of the control and interventional drugs for about seven (7) hours after initiation of the control and interventional drugs.

Results:

At the conclusion of the study, 30 day mortality is assessed.

According to an embodiment of the present teachings, a method of treating a patient suffering from low blood pressure is provided. The patient can suffer from one of septic shock, acute kidney injury, severe hypotension, and refractory hypotension, but not from myocardial infarction. The method can comprise administering a therapeutically effective dose of Angiotensin II ("Ang II") to the patient.

The dose of Angiotensin II can be administered at a rate of between about 5 ng/kg/min to about 100 ng/kg/min. The dose of Angiotensin II can be administered at a rate of between about 10 ng/kg/min to about 50 ng/kg/min. The dose of Angiotensin II can be administered at a rate of between about 20 ng/kg/min to about 40 ng/kg/min.

The dose administration can last from about 0.25 hours to about 120 hours. The dose administration can last from about 1 hour to about 7 hours. The dose administration can last from about 2 hour to about 6 hours. The dose administration can last from about 3 hours to about 5 hours.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

The following publications are herein incorporated by reference in their entireties:

1. Bagshaw S M, George C, Dinu I, Bellomo R: A Multi-Centre Evaluation of the Rifle Criteria for Early Acute Kidney Injury in Critically Ill Patients. Nephrol Dial Transplant October 25 (Epub): 2007
2. Uchino S, Kellum J A, Bellomo R, Doig G S, Morimatsu H, Morgera S, Schetz M, Tan I, Bouman C, Macedo E, Gibney N, Tolwani A, Ronco C: Acute renal failure in critically ill patients: a multinational, multicenter study. JAMA 294:813-818, 2005
3. Heringlake M, Knappe M, Vargas H O, et al: Renal dysfunction according to the ADQI-RIFLE system and clinical practice patterns after cardiac surgery in Germany. Minerva Anestesiol 72:645-654, 2006
4. Kuitunen A, Vento A, Suojaranta-Ylinen R, Pettila V: Acute renal failure after cardiac surgery: evaluation of the RIFLE classification. Ann Thorac Surg 81:542-546, 2006
5. Lopes J A, Jorge S, Resina C, et al: Prognostic utility of RIFLE for acute renal failure in patients with sepsis. Crit Care 11:408, 2007
6. Wilson C T, Fisher E S, Welch H G, Siewers A E, Lucas F L: U.S. trends in CABG hospital volume: the effect of adding cardiac surgery programs. Health Aff 26:162-168, 2007
7. Angus D C, Linde-Zwirble W T, Lidicker J, Clermont G, Carcillo J, Pinsky M R: Epidemiology of severe sepsis in the United States: Analysis of incidence, outcome, and associated costs of care. Crit Care Med 29:1303-1310, 2001

What is claimed is:

1. A method of increasing blood pressure in a human subject having septic shock and in need of said increasing, comprising administering Angiotensin 11 to the human subject at an initial rate of about 20 ng/kg/min.

2. The method of claim 1, further comprising titrating the rate up to about 30 ng/kg/min.

3. The method of claim 1, further comprising titrating the rate up to about 40 ng/kg/min.

4. The method of claim 1, wherein the rate is titrated up one or more times by about 10 ng/kg/min.

5. The method of claim 1, wherein the Angiotensin II is administered to the human subject over a period of about 0.25 hours to about 120 hours.

6. The method of claim 5, wherein the Angiotensin II is administered to the human subject over a period of about 1 hour to about 7 hours.

7. The method of claim 1, wherein the rate of administration of Angiotensin II is titrated to achieve a mean arterial pressure of about 65 mmHg.

8. The method of claim 1, wherein the rate of administration of Angiotensin II is titrated to achieve a mean arterial pressure of 65 mmHg.

9. The method of claim 7, wherein the mean arterial pressure is maintained at about 65 mmHg for about 0.25 hours to about 120 hours.

10. The method of claim 9, wherein the mean arterial pressure is maintained at about 65 mmHg for about 1 hour to about 7 hours.

11. The method of claim 1, wherein the human subject is undergoing treatment with one or more vasopressors.

12. The method of claim 11, wherein the one or more vasopressors is selected from the group consisting of norepinephrine, vasopressin, epinephrine, and dopamine.

13. The method of claim 12, wherein the one or more vasopressors is norepinephrine.

14. The method of claim 12, wherein the one or more vasopressors is vasopressin.

15. The method of claim 11, further comprising titrating the rate up to about 30 ng/kg/min.

16. The method of claim 11, further comprising titrating the rate up to about 40 ng/kg/min.

17. The method of claim 11, wherein the rate is titrated up one or more times by about 10 ng/kg/min.

18. The method of claim 11, wherein the Angiotensin II is administered to the human subject over a period of about 0.25 hours to about 120 hours.

19. The method of claim 18, wherein the Angiotensin II is administered to the human subject over a period of about 1 hour to about 7 hours.

20. The method of claim 11, wherein the rate of administration of Angiotensin II is titrated to achieve a mean arterial pressure of about 65 mmHg.

21. The method of claim 11, wherein the rate of administration of Angiotensin II is titrated to achieve a mean arterial pressure of 65 mmHg.

22. The method of claim 20, wherein the mean arterial pressure is maintained at about 65 mmHg for about 0.25 hours to about 120 hours.

23. The method of claim 22, wherein the mean arterial pressure is maintained at about 65 mmHg for about 1 hour to about 7 hours.

24. A method of increasing blood pressure in a human subject having septic shock and in need of said increasing, comprising administering Angiotensin 11 to the human subject at a rate of from about 20 ng/kg/min to about 40 ng/kg/min.

25. The method of claim 24, wherein the Angiotensin II is administered at a rate of about 30 ng/kg/min.

26. The method of claim 24, wherein the Angiotensin II is administered at a rate of about 40 ng/kg/min.

* * * * *